(12) United States Patent
Björling

(10) Patent No.: US 8,103,344 B2
(45) Date of Patent: Jan. 24, 2012

(54) METHOD, DEVICE, IMPLANTABLE STIMULATOR AND DUAL CHAMBER CARDIAC THERAPY SYSTEM

(75) Inventor: Anders Björling, Solna (SE)

(73) Assignee: St. Jude Medical AB, Jarfalla (SE)

( * ) Notice: Subject to any disclaimer, the term of this patent is extended or adjusted under 35 U.S.C. 154(b) by 259 days.

(21) Appl. No.: 12/446,496

(22) PCT Filed: Oct. 31, 2006

(86) PCT No.: PCT/SE2006/001229
§ 371 (c)(1),
(2), (4) Date: Apr. 21, 2009

(87) PCT Pub. No.: WO2008/054261
PCT Pub. Date: May 8, 2008

(65) Prior Publication Data
US 2010/0305640 A1    Dec. 2, 2010

(51) Int. Cl.
*A61N 1/00* (2006.01)
(52) U.S. Cl. .......................................................... 607/14
(58) Field of Classification Search ................ 600/516, 600/517; 607/14, 17, 18
See application file for complete search history.

(56) References Cited

U.S. PATENT DOCUMENTS

| | | | |
|---|---|---|---|
| 4,802,483 | A | 2/1989 | Lindgren |
| 5,628,777 | A | 5/1997 | Moberg et al. |
| 5,893,882 | A | 4/1999 | Peterson et al. |
| 6,567,691 | B1 | 5/2003 | Stadler |
| 6,571,130 | B1 | 5/2003 | Ljungström et al. |
| 6,776,411 | B2 | 8/2004 | Klenk |
| 7,149,587 | B2 | 12/2006 | Wardle et al. |
| 7,509,169 | B2 | 3/2009 | Eigler et al. |
| 2003/0083702 | A1* | 5/2003 | Stadler et al. ............ 607/14 |
| 2004/0133245 | A1 | 7/2004 | Norén |
| 2004/0138715 | A1 | 7/2004 | Van Groeningen et al. |
| 2005/0209649 | A1 | 9/2005 | Ferek-petric |
| 2006/0281998 | A1* | 12/2006 | Li ............................ 600/516 |
| 2007/0055115 | A1 | 3/2007 | Kwok et al. |
| 2007/0129643 | A1 | 6/2007 | Kwok et al. |

FOREIGN PATENT DOCUMENTS
WO    WO 2005/018737    3/2005

\* cited by examiner

*Primary Examiner* — George Manuel
*Assistant Examiner* — Robert Wieland
(74) *Attorney, Agent, or Firm* — Schiff Hardin LLP (57) ABSTRACT

In a device and method in a dual chamber pacing system operating in an atrial synchronized mode, the cardiac stimulator is connectable to a lead arrangement arranged for sensing atrial electrical and mechanical activity. Upon detection of an atrial arrhythmia based on either of sensed atrial mechanical activity, atrial electrical activity, or a combination thereof, a mode switch from an atrial synchronized ventricle stimulating mode to a non-atrial synchronized mode is triggered.

25 Claims, 7 Drawing Sheets

METHOD, DEVICE, IMPLANTABLE STIMULATOR AND DUAL CHAMBER CARDIAC THERAPY SYSTEM

BACKGROUND OF THE INVENTION

1. Field of the Invention

The present invention generally relates to the field of implantable heart stimulation devices, such as pacemakers, implantable cardioverter-defibrillators (ICD), and similar cardiac stimulation devices. More specifically, the present invention relates to an implantable cardiac stimulator arranged for dual chamber pacing in a first mode with atrial ventricular synchronized stimulation, comprising mode switch means for switching from the first mode to a second mode without atrial ventricular synchronized stimulation.

2. Description of the Prior Art

In a dual chamber pacing system, e.g. a DDD-R system, atrial events are tracked for ventricular stimulation synchronization. The purpose is to mimic the behavior of a healthy heart, where the natural ventricular contractions are synchronized with atrial contractions, and to thereby obtain a physiologically optimized ventricular stimulation. However, the pacing system should not track the atrial activity during atrial tachyarrhythmias, since an atrial synchronized ventricular stimulation would not meet the physiological needs of the patient. The pacing mode should in this case be changed to a non-atrial tracking mode, such as VVI-R, where physiologically adequate stimulation therapy would be provided, albeit not physiologically optimized.

Cardiac stimulators are known in the art which are provided with a mode switching feature adapted to stabilize the ventricular heart rate during atrial fibrillation or other atrial condition where atrial tracking is not appropriate. In response to a detection of atrial fibrillation, such a stimulator therefore switches into a non-atrial synchronized ventricular rate stabilization pacing mode. The stimulator remains in this mode of operation as long as the atrial fibrillation prevails.

The detection of atrial tachyarrhythmia, such as atrial tachycardia (AT), atrial fibrillation (AF), atrial flutter or supraventricular tachycardia (SVT), is generally obtained from an atrial electrogram (IEGM). In order to avoid unfounded triggering of mode switch, the detection algorithms are generally set such that the atrial tachyarrhythmia must persist for a period of time before it is reliably detected and a mode switch is triggered. This is also generally the case for the opposite situation, i.e. when a stabilization of atrial behavior is determined and a mode switch back to atrial tracking is triggered. Thus, the atrial tachyarrhythmia must be absent for a certain period of time before a return to atrial tracking mode is triggered.

Furthermore, in order to avoid over-sensing, that is to erroneously indicate atrial tachyarrhythmia for triggering a mode switch, the detection thresholds are often set high in order to increase specificity. However, this often results in under-sensing, which is failure to detect actual atrial tachyarrhythmia that could, and for the benefit of the patient often should, result in a mode switch. One particular instance where the risk of under-sensing is apparent is the occurrence of atrial fibrillation, AF. This is mainly due to the fact that the amplitude of the IEGM is very low during AF. Thus, the AF condition, as well as other tachyarrhythmia conditions, may go undetected.

An effect of having a delay between the onset of atrial tachyarrhythmia and the triggering of a switch to a non-atrial tracking mode is that fast atrial rhythms may be conduced to the ventricles and result in an unphysiologically fast ventricular rhythm. Obviously, this may be unpleasant for the patient. Furthermore, the delay in mode switch back to atrial tracking may result in a period of undesired physiologically inadequate pacing therapy.

If the detection and triggering algorithms were to be set such that the delay is significantly shortened, the above problems could be reduced. However, the chance of unwarranted mode switch would increase, which would not be beneficial in terms of optimizing pacing therapy with a stable and physiologically correct atrial behavior. Consequently, there exists is a trade-off between speed and specificity of mode switch triggering.

Thus, there is a need for improved mode switch triggering algorithms which reduces mode switch delays without sacrificing specificity in atrial tachyarrhythmia determination.

SUMMARY OF THE INVENTION

Thus, an object of the present invention is to provide an improved device and method for mode switching in a dual chamber cardiac stimulator.

This and other objects are achieved by a device, a cardiac stimulator, a system, and a method as claimed in the independent claims. Further embodiments are defined in the dependent claims.

According to one aspect, there is provided a device for a dual chamber cardiac stimulator for controlling the delivery of stimulation pulses to a human heart, wherein the stimulator is connectable to a lead arrangement arranged for sensing atrial electrical activity and atrial mechanical activity. The device has processing circuitry arranged for receiving a first signal representative of atrial electrical activity, and a second signal representative of atrial mechanical activity, determining if the electrical activity indicates atrial tachyarrhythmia, if the mechanical activity indicates atrial tachyarrhythmia, and if a combination of said electrical and mechanical activity indicates atrial tachyarrhythmia. The processing circuitry is further arranged for effectuating a mode switch, as soon as either of the electrical, mechanical, or combination of electrical and mechanical activity indicates atrial tachyarrhythmia, from a first mode where delivery of ventricular stimulation pulses is synchronized with detected atrial events, to a second mode where delivery of ventricular stimulation pulses is unsynchronized with detected atrial events.

According to another aspect, there is provided an implantable dual chamber cardiac stimulator for delivering dual chamber stimulation pulses to a human heart. The stimulator comprising a pulse generator for generating said stimulation pulses, control circuitry for controlling the delivery of said stimulation pulses to the heart, the control circuitry being operable in a first mode where delivery of ventricular stimulation pulses is synchronized with detected atrial events, and in a second mode where delivery of ventricular stimulation pulses is not synchronized with detected atrial events. The stimulator is connectable to a cardiac lead arrangement for conduction of stimulation pulses to the heart and sensed cardiac electrical activity from the heart, the lead arrangement further being arranged for sensing atrial electrical activity and atrial mechanical activity. The stimulator further has a device as described in the above paragraph.

According to a third aspect, there is provided a dual chamber cardiac therapy system for delivering stimulation pulses to a human heart. The system has an implantable cardiac stimulator as mentioned in the above paragraph, and a cardiac lead arrangement for conducting said stimulation pulses to the heart, and for conducting electrical signals from the heart to the control circuitry, the lead arrangement having an implantable lead arranged for sensing atrial electrical activity and atrial mechanical activity.

According to a fourth aspect, there is provided a method for detecting an atrial arrhythmia for activating a pacing mode switch in a dual chamber cardiac stimulator. The method includes the steps of receiving a first signal representative of atrial electrical activity, and a second signal representative of atrial mechanical activity, determining if the electrical activity indicates atrial tachyarrhythmia, if said mechanical activity indicates atrial tachyarrhythmia, and if a combination of said electrical and mechanical activity indicates atrial tachyarrhythmia. The method includes the step of effectuating a mode switch, as soon as either of said electrical, mechanical, or combination of electrical and mechanical activity indicates atrial tachyarrhythmia, from a first mode where delivery of ventricular stimulation pulses is synchronized with detected atrial events, to a second mode where delivery of ventricular stimulation pulses is unsynchronized with detected atrial events.

According to a fifth aspect, there is provided a computer program product, directly loadable into an internal memory of an implantable medical device, comprising software code portions for causing the implantable medical device to perform steps in accordance with the above method.

It should be noted that, for the purposes of this application, "atrial electrical activity" refers to any detectable electrical signals or potential variations that is related to atrial tissue, such as atrial tissue depolarizations; and that "atrial mechanical activity" relates to any detectable mechanical entities related to atrial tissue, such as atrial pressures, atrial tissue movements, and atrial contractions.

Furthermore, in the following, it is generally stated that a mode switch is effectuated or ensues after an indication of atrial tachyarrhythmia has been determined. This refers to a mode switch away from an atrial tracking mode upon atrial tachyarrhythmia indication, as readily understood by those of ordinary skill in this field. Of course, as also understood by the skilled person, if the stimulator already operates in a non-atrial tracking mode upon said indication of atrial tachyarrhythmia, no mode switch has to be effectuated. Thus, even where not explicitly stated in the following, the effectuation of a mode switch is conditioned by the present operating mode, i.e. atrial tracking or non-atrial tracking mode.

Thus, the present invention is based on the advantageous idea of using information related to both atrial electrical as well as mechanical activity for determining indications of atrial tachyarrhythmia, and for subsequently effectuating a mode switch from an atrial tracking mode to a non-atrial tracking mode if either of obtained mechanical, electrical or combination of mechanical and electrical activity information indicates atrial tachyarrhythmia. Thereby, a quick and specific determination of atrial tachyarrhythmia is obtained, resulting in a corresponding quick and reliable triggering and performing of mode switch to a non-atrial tracking mode.

By having several related but independently detectable atrial activities monitored, i.e. atrial mechanical and atrial electrical activity, the specificity may be increased without sacrificing speed, and vice versa. In other words, the thresholds for detection of atrial tachyarrhythmia (AT) and triggering of mode switch may be increased to or maintained at a high level for each of the detection criteria, thereby providing a high specificity of AT determination. However, by adding detection criteria, the chances of either of the detection criteria, i.e. the mechanical activity criterion, the electrical activity criterion, or the combined mechanical and electrical activity criterion, is significantly higher than if only one of the criteria was to be used.

Consequently, if a detected electrical activity indicates atrial tachyarrhythmia, then a mode switch may be effectuated. Likewise, if a detected mechanical activity indicates atrial tachyarrhythmia, then a mode switch may also be actuated. For both of these criteria, the threshold value for determining AT from the detected activity may be set high, thereby maintaining a high specificity. By the mere provision of two different criteria, both fulfilling high specificity requirements, an increase in the speed for mode switch triggering will be obtained.

However, further threshold conditions may be added for each of the two criteria, which may be set at a lower or much lower level, for enabling more rapid triggering of the mode switch. But instead of using the lower threshold criteria for triggering a mode switch in itself, the criteria may be used as a trigger for turning to another criterion in order to confirm the indication of atrial tachyarrhythmia. In other words, a determination of possible atrial tachyarrhythmia indication for one of the criteria triggers a particular detection algorithm for the other criteria.

A number of different embodiments are contemplated in determining indication of atrial tachyarrhythmia, both in terms of indicating tachyarrhythmia from solely atrial electrical or mechanical activity, respectively, as well as from combining information obtained from atrial electrical and mechanical activity. As understood by the person skilled in the art, a vast number of different algorithms may be used for this determination, a few of which will be described in the following.

Firstly, turning to criteria for indicating atrial tachyarrhythmia based on electrical activity alone, use can be made of an atrial IEGM signal, which is generally used in state of the art dual chamber stimulators. As one example, an atrial rate may be determined from the IEGM signal and compared to a selected threshold value. If the rate exceeds the threshold value, atrial tachyarrhythmia is indicated, which triggers an ensuing mode switch. The threshold value is preferably selected in adaptation to the physiology and heart condition of the particular patient. As an example, the threshold value could be set to somewhere between 130 and 200 atrial beats per minute, where the lower threshold values would for example be used for elderly patients. Furthermore, the detection algorithm could include a chosen number of successive atrial beats for improving the specificity of the algorithm. As an example, the algorithm could use the information from 3-10 successive atrial beats before a mode switch is triggered. If the threshold for indicating atrial tachyarrhythmia is between 130 and 200 atrial beats per minute, mode switch would be effectuated within approximately 1 to 4 seconds after atrial tachyarrhythmia onset.

Use can in this context be made of atrial tachyarrhythmia detection methods, based solely on an obtained IEGM signal, used in cardiac stimulators or otherwise known within the art today. Thus, the present invention is not restricted to the particular example of IEGM based detection method described here.

Secondly, turning to criteria for indicating atrial tachyarrhythmia based on mechanical activity alone, use can be made of a mechanical activity signal mainly related to contractions of the atrium. During AF, the occurrences of atrial contractions are essentially completely ceased, which means that use can be made of the fact that there are no significant mechanical activities in the atrium. According to one embodiment for indicating atrial tachyarrhythmia from mechanical activity, a frequency or rate is calculated from an obtained mechanical activity signal. The frequency is related to atrial contraction, e.g. pressure variations or cardiac wall movements representative of atrial contraction. In similar manner as described above in relation to using IEGM rate as an indicator of atrial tachyarrhythmia, the calculated mechanical frequency may be compared to a selected threshold value. If the rate exceeds the threshold value, atrial tachyarrhythmia is indicated, which triggers an ensuing mode switch. The selected threshold values could then preferably be similar to those mentioned above, i.e. between 130 and 200 atrial beats per minute depending on the physiology and cardiac disorder of the particular patient.

Alternatively or additionally, the atrial tachyarrhythmia detection algorithm checks if this frequency falls below a selected threshold value, that is if the variations in atrial mechanical activity occur too seldom. This is for instance the case when the atrium does not function as it should and is not capable of generating enough pressure pulses or cardiac wall movements, such as during atrial fibrillation.

The mechanical activity information obtained so far could in itself be used for indicating atrial tachyarrhythmia. Alternatively, the algorithm could then check if the average atrial mechanical activity is too low, e.g. an average atrial pulse amplitude. Possibly, the threshold level for sensing mechanical activity may have been set too high so that even though the patient is in normal sinus rhythm, a low rate is detected. If so, then the average mechanical activity should be within normal ranges and not too low. The term average mechanical activity could refer to an average pulse pressure during a selected period, or an average acceleration related to cardiac wall movements measured during a selected period. If it is considered normal, an atrial tachyarrhythmia will not be indicated and no mode switch will be triggered.

It should be noted that the means and algorithms for determining electrical frequency and mechanical frequency, i.e. related to a mere determination of atrial beats per minute, are known in the art and are not described further herein. An example of using atrial electrical activity for indicating atrial tachyarrhythmia for triggering a mode switch is shown in U.S. Pat. No. 5,549,649, the contents of which is incorporated herein in its entirety.

It should also be noted that even though they are described separately, the algorithms described below and above could also be used in conjunction. In other words, a cardiac stimulator could comprise processing circuitry arranged to perform any selected atrial tachyarrhythmia detection method described herein, or any combination of the atrial tachyarrhythmia detection methods described herein. For instance, processing circuitry may be arranged for performing a plurality of atrial tachyarrhythmia detection methods utilizing a combination of mechanical and electrical activity information.

Thirdly, turning to criteria for indicating atrial tachyarrhythmia based on both detected electrical and mechanical activity, a few exemplifying embodiments will be presented. According to one embodiment, an atrial electrical frequency or rate and an atrial mechanical frequency or rate is calculated. The obtained mechanical and electrical frequencies are then compared to each other. If the quotient therebetween falls outside a predetermined threshold range, which could be an open range with one threshold value or a closed range with two threshold values, an atrial tachyarrhythmia is indicated and an ensuing switch to non-atrial tracking mode is effectuated.

If atrial fibrillation arises, and the amplitude of electrical activity is too low for sensing and triggering of an ensuing ventricular stimulation, then the cardiac stimulator will start to stimulate the ventricle at the base rate or at another sensor indicated rate. The ventricular events occurring through said base rate pacing, although not sensed for triggering ventricular stimulation, may still be part of the electrical activity information from which an electrical frequency, i.e. IEGM rate, is calculated. Thus, even though the stimulator has not sensed any electrical atrial events during AF, the IEGM rate will, due to the ventricular events showing in the IEGM, still be higher than the atrial mechanical frequency, which will then be zero or at least very low. Consequently, even if the electrical frequency is calculated from an IEGM representing only ventricular events, an atrial tachyarrhythmia will still be indicated and an ensuing mode switch effectuated.

Turning to another embodiment where a combination of mechanical and electrical activity information is utilized, this embodiment is based on the appearance of a signal representative of mechanical activity. First, said signal is obtained and the morphology of the signal is determined, or specific characteristics of the signal are determined. Then, it is determined if the signal is acceptable or normal. This can be done using a reference template, typical reference characteristics, reference values or similar reference information, which has been acquired when the patient is confirmed to be in normal sinus rhythm. A short sequence, preferably 2-5 seconds is studied. If the signal deviates from the reference representing a normal or accepted signal, then the electrical activity signal, e.g. IEGM rate is studied in more detail.

The studied period electrical activity may differ somewhat to the sequence during which the mechanical activity has been studied. In order not to delay the determination of indicated tachyarrhythmia, use can be made of a time period backwards, e.g. the latest 3 to 10 seconds. Alternatively, a forward time period or a combination of forward and backward time period is studied, which may be in the range of 3 to 10 seconds. If the IEGM rate during the studied period exceeds a chosen threshold value, or exhibits lack in regularity, atrial tachyarrhythmia is indicated and a mode switch is performed. The regularity check is mainly used for the fact that a known characteristic of atrial fibrillation is its variable signal amplitude, which often results in a detected irregular electrical rate, i.e. not all oscillations are detected.

If the calculated electronic frequency does not exceed a chosen threshold or exhibits considerable irregularity, then a check against a lower threshold is performed in order too determine if the electronic frequency is very low or if it is zero, i.e. no detections of electrical activity is made. If so, then the cause may be so-called "fine AF", that is atrial fibrillation with a very low amplitude, or even atrial standstill. In order for differentiation between these two, the IEGM signal is searched for low amplitude "ripple" which is present during AF and not during standstill. This could for example be done by studying the standard deviation of the IEGM signal. If the standard deviation of the IEGM is higher than normal, this would indicate an atrial tachyarrhythmia in the form of fine AF and a mode switch is performed. Alternatively, the lower threshold could be set at an even lower level at which fine AF ripple could be sensed. If significant electrical activity is determined with this lower threshold, then AF is indicated and mode switch is performed.

According to a further embodiment, an IEGM signal is first obtained. The P wave of the IEGM signal is then detected, and a mechanical activity detection window is opened. If during this detection window, no mechanical activity is detected which would correspond to mechanical contraction of the atrium, then an atrial arrhythmia is indicated and mode switch is performed. Preferably, the algorithm performs this determination of lacking atrial contraction for a subsequent number of P waves, such as two to five successive P waves, before an indication of atrial arrhythmia is determined and mode switching effectuated.

In a further example, the determination may be made for a period corresponding to a selected number of subsequent P waves, and atrial arrhythmia may be determined in the absence of at least a specified number of atrial contraction responses. For instance may three non-occurrences of atrial contraction responses in five successive P waves be sufficient for indicating atrial tachyarrhythmia.

In further embodiments of the present invention, following a mode switch from an atrial tracking mode to a non-atrial tracking mode, the atrial electrical and mechanical activity is continuously monitored in order to assess when a return to atrial tracking mode is appropriate. According to these embodiments, a mode switch back to atrial tracking mode is performed when none of the atrial mechanical, electrical or combination of mechanical and electrical activity indicates atrial tachyarrhythmia. In other words, as long as at least one of the atrial tachyarrhythmia detecting algorithms using information of atrial mechanical or electrical activity, or a combination thereof, the cardiac stimulator will remain in a non-atrial tracking mode.

It should in this context be noted that further criteria may be used as an indicator when a mode switch back to atrial tracking should be performed. Thus, when all of the atrial arrhythmia detecting algorithms indicate stable atrial activity, a further check for the appropriateness of atrial tracking may be determined, such as the heart rate falling below a chosen rate, or the atrial rate being within a selected range.

According to specific embodiments, the atrial mechanical activity may be atrial pulse pressure, or more specifically changes in atrial pulse pressure, for indicating contractions of atrial tissue. Such pressure could be detected or measured with a pressure sensor arranged in or at an atrium of the heart. As an example, use may be made of a pressure sensor as disclosed in International Application published under WO 2005/107583 A2, or as disclosed in U.S. Pat. Nos. 6,571,130 and 6,776,411, which are incorporated herein in their entirety. Alternatively, use may be made of any other sensor suitable for measuring atrial pressure.

According to other embodiments, the atrial mechanical activity may be atrial wall movements, which would indicate atrial contractions. Such atrial wall movements could be detected using an accelerometer positioned at an appropriate location in or at atrial wall tissue. Such an accelerometer is preferably positioned within the atrium, but an additional extracardiac accelerometer is also contemplated. The extracardiac accelerometer may then be used for detecting body movements of the patient for compensation of artifacts in the intracardiac accelerometer signal due to such body movements.

Furthermore, according to preferred embodiments, the detection algorithms for indicating atrial tachyarrhythmia are enabled at all times. Consequently, a sensor for sensing mechanical activity used by the processing circuitry for performing said algorithms is also enabled at all times.

Further objects and advantages of the present invention will be discussed below by means of exemplifying embodiments.

DESCRIPTION OF THE PREFERRED EMBODIMENTS

The following is a description of exemplifying embodiments in accordance with the present invention. This description is intended for describing the general principles and specific embodiments of the invention and is not to be taken in a limiting sense. Thus, even though a biventricular heart stimulator will be described, the invention is also applicable to dual chamber stimulators with ventricular stimulation in one ventricle only. Furthermore, the invention is not restricted to pacemakers, but to any sort of cardiac stimulators having dual chamber pacing capability, such as implantable cardioverter defibrillators (ICD). The invention is also applicable to systems where only atrial sensing, not pacing, is provided. Please note that like reference numerals indicate structures or elements having same or similar functions or constructional features.

Figure 1:
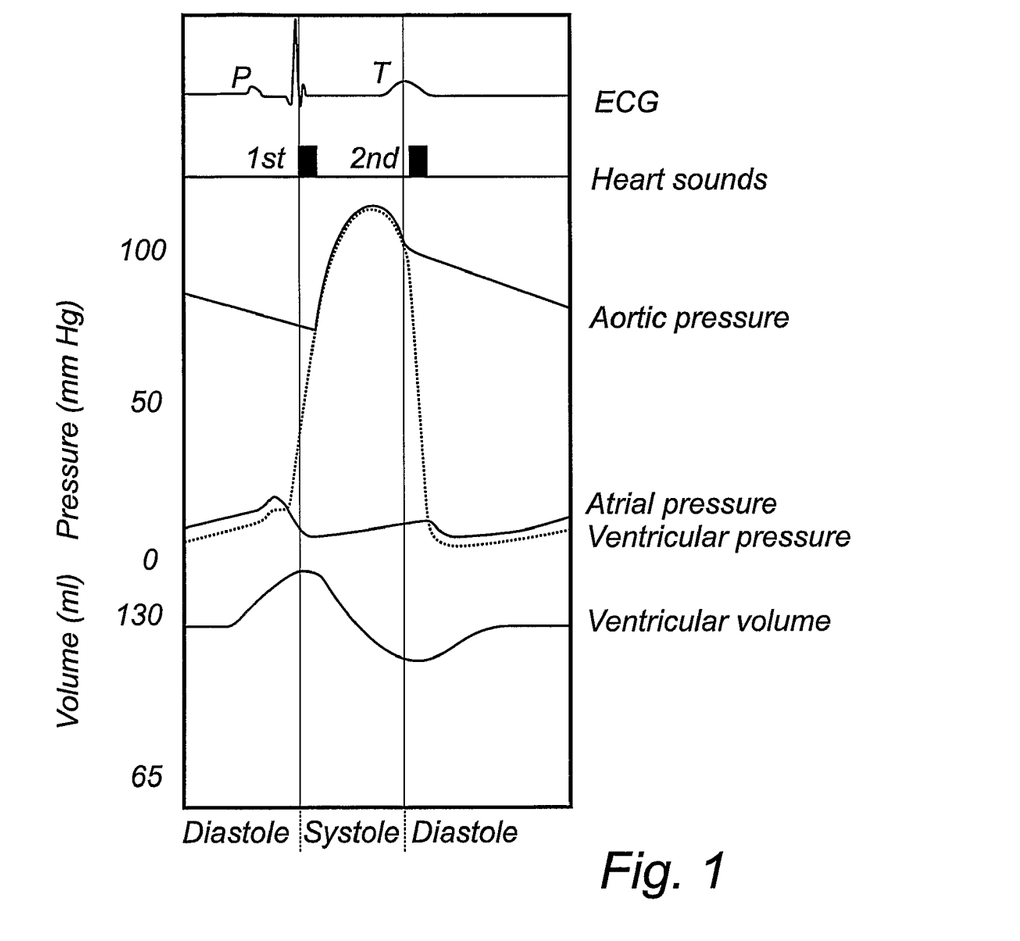
FIG. 1 is a schematic illustration of the correlation between different cardiac events and mechanical and electrical activity.

With reference first to FIG. 1, there is shown a schematic illustration of the relationships between different electrical and mechanical events occurring during a cardiac cycle. Going from top to bottom, an electrogram signal is indicated. Even though an IEGM does not have exactly the same appearance, the essential portions may still be deduced. Evidently, the ECG signal comprises a P wave representing a depolarization of the atria, a QRS complex representing the depolarization of the ventricles, and a T wave representing the repolarization of the ventricles. In this figure, for illustrational purposes, only the P wave and the T wave has been indicated.

Below the ECG, the occurrences of the heart sounds is indicated. The 1st occurrence results from the closure of the mitral and tricuspid valves, and the 2nd occurrence results from a closure of the aortic and pulmonary valves. Thereafter, the pressure variations of the heart is shown, including the pressures of the aorta, atrium, and ventricle, as well as ventricular volume. Finally, the diastolic and systolic phases of the cardiac cycle is indicated at the bottom of the figure.

As clearly indicated, the atrial pressure, which is in this context considered a mechanical activity, varies over the heart cycle. Thus, by monitoring the changes in atrial pressure, atrial rate can be determined. Furthermore, atrial pressures are indicative of atrial contractions, whereby the absence or significant atrial decrease of pressure variations, can be used as an indicator absent atrial contractions.

Likewise, atrial wall movements may be detected, for instance using an accelerometer positioned at or in cardiac wall tissue. By monitoring the changes in atrial wall movements, atrial rate can be determined. Furthermore, the amplitude of the cardiac wall movements may be used for determining cardiac contractions and for classifying between different atrial conditions. Preferably, a further accelerometer is used, which is located at a position away from the heart, suitably in an implanted stimulator. Then, the extracardiac accelerometer can be used for detecting body movements of the patient for compensation of artifacts in the intracardiac accelerometer signal due to such body movements.

It should be noted that due to the difference in magnitude between atrial and ventricular contractions, occurrences of ventricular contractions could be sensed and have an impact on the atrial pressure. Thus, even during absence of atrial contractions, slight pressure variations in the atrium may still be detected, which variations are related to ventricular contractions. However, by correlating those pressure changes with sensed ventricular pressure changes, aortic pressure, the QRS complex of the ECG, detected heart sounds, or any other physical occurrence which is correlated with the heart cycle, such influences on the detected atrial pressure may be compensated for. For the same reason, during detection of cardiac wall movements, slight movements may still be detected at atrial fibrillation or the like, even though the atrium is absent of atrial contractions. Again, such detected movements may easily be compensated for.

Comparing the ECG signal with the atrial pressure signal, it is clear that the P wave is immediately followed by an increase in the atrial pressure. This is because the P wave represents atrial depolarization, which results in a contraction of atrial tissue that, in turn, increases the atrial pressure. Thus, by monitoring the P wave in combination with the atrial pressure, the presence or absence of mechanical contraction response on atrial electrical signal, i.e. depolarization, may be determined.

Figure 2:
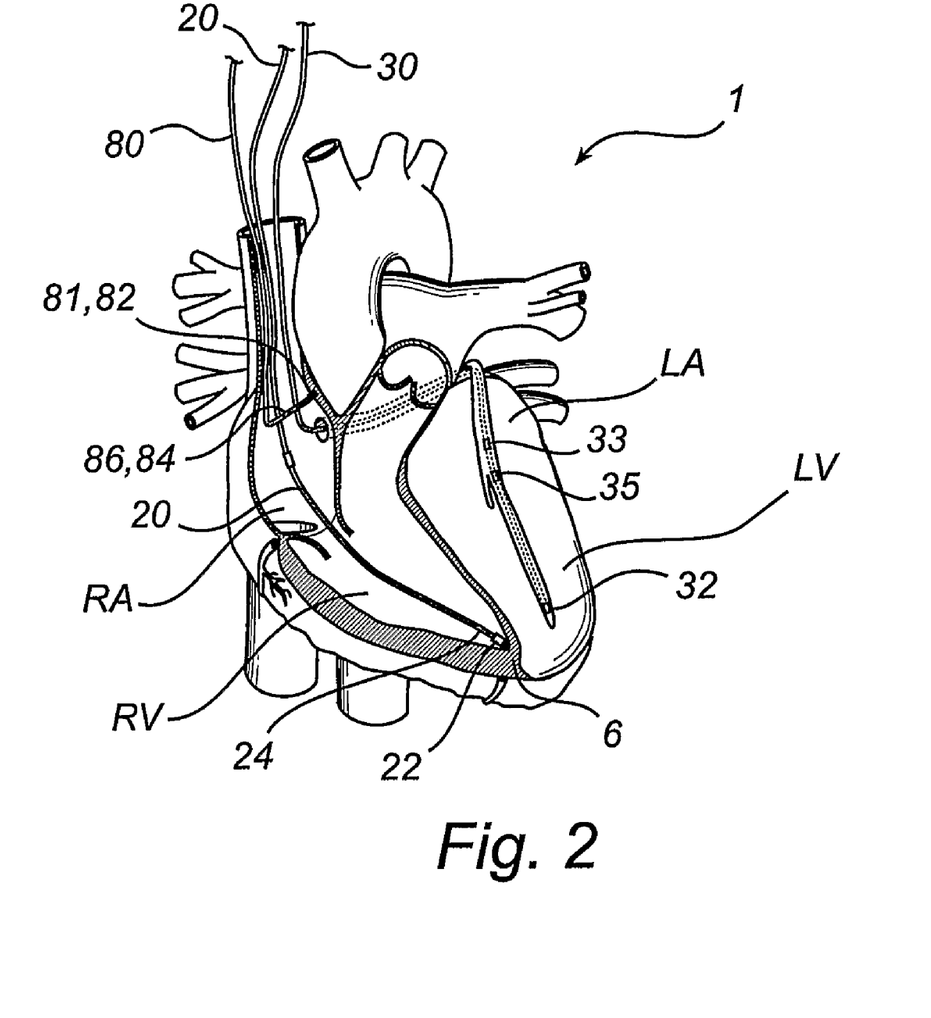
FIG. 2 is a partly cut-away view of a human heart provided with leads and sensors according to exemplifying embodiments.

With reference now to FIG. 2, there is shown a patient's heart 1 in electrical communication with a stimulation device by way of two leads 20 and 30 suitable for delivering multi-chamber stimulation (and possible shock therapy). The illustrated portions of the heart 1 include the right atrium RA, the right ventricle RV, the left atrium LA, the left ventricle LV, and the apex 6. Furthermore, the placement of cardiac leads, cardiac electrodes and sensors for sensing atrial wall movements are illustrated.

In order to sense right ventricular cardiac signals and to provide stimulation therapy to the right ventricle RV, the stimulation device 10 is coupled to an implantable right ventricular lead 20 having a ventricular tip electrode 22, and a ventricular annular or ring electrode 24. The ring electrode 24 is arranged for sensing electrical activity, intrinsic or evoked, in the right ventricle RV. The right ventricular tip electrode 22 is arranged to be implanted in the endocardium of the right ventricle, e.g. near the apex 6 of the heart.

In order to sense left ventricular cardiac signals and to provide pacing therapy for the left ventricle LV, the stimulation device 10 is coupled to a "coronary sinus" lead 30 designed for placement via the coronary sinus in veins located distally thereof, so as to place a distal electrode adjacent to the left ventricle. Also, additional electrode(s) 35 could thereby be positioned adjacent to the left atrium. The coronary sinus lead 30 is designed to receive ventricular cardiac signals from the cardiac stimulator 10 and to deliver left ventricular LV pacing therapy using at least a left ventricular tip electrode 32 to the heart 1. In this example, the LV lead 30 comprises an annular ring electrode (not shown) for sensing electrical activity related to the left ventricle LV of the heart.

In FIG. 2, the RV and LV leads 20, 30 have been supplemented with a right atrial RA lead 80. The lead comprises an RA tip electrode 82 positioned in the patient's right atrial appendage for delivering electrical stimuli to the right atrium, and an RA ring electrode 84 for sensing and conducting cardiac signals from the right atrium to the cardiac stimulator. Furthermore, an RA pressure sensor 86 is provided next to the RA ring electrode 84 for detecting and measuring pressure RA pressure variations. Also, a cardiac wall motion sensor 81 is provided at the RA tip electrode 82 for sensing cardiac wall movements of the RA wall. Furthermore, the LV lead 30 is provided with an additional atrial wall movement sensor 33, as well as an additional atrial stimulating electrode 35, of the ring type, arranged distally of the movement sensor 33. Said additional atrial electrode 35 could alternatively be used for sensing atrial electrical activity related to the left atrium.

It should be noted that, for ease of illustration, both an atrial wall motion sensor 81, as well as an atrial pressure sensor 86 are illustrated in the same figure. However, the dual chamber pacing system according to preferred embodiments of the invention has either a pressure sensor or an atrial wall motion sensor, preferably an accelerometer, in the right atrium and/or at the left atrium.

Even though a particular example have been illustrated in FIG. 2, the invention is not restricted to the illustrated example of lead, electrode and sensor placement. For instance, in the illustrated example, the wall motion sensors are of accelerometer type. However, other types of sensors for sensing and measuring wall movements are to be comprised in the scope of the present application.

Figure 3:
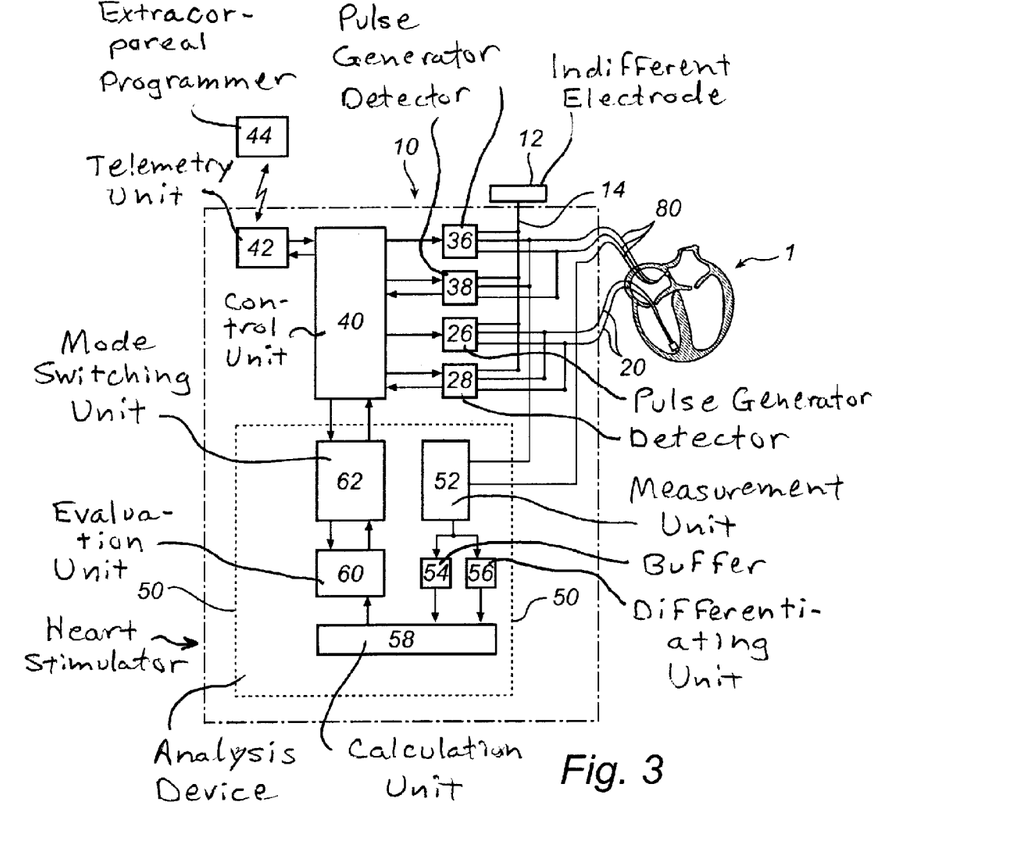
FIG. 3 is an illustration in block diagram form of an implantable stimulator.

Turning now to FIG. 3, the heart stimulator 10 is shown in a block diagram form. For illustrative purposes, reference is made to FIG. 2 for the elements of the leads that are intended for positioning in or at the heart. Furthermore, even though a dual chamber stimulator with univentricular stimulation is shown for ease of illustration, the following description is also applicable and relevant for embodiments of a biventricular stimulator.

The heart stimulator 10 is connected to a heart 1 in order to sense heart signals and emit stimulation pulses to the heart 1. A first tip electrode 22 is anchored in the right ventricle RV of the heart 1 and connected, via a first electrode conductor in the lead 20, to a first pulse generator 26 in the heart stimulator 10. A first ring electrode 24 is connected near the first tip electrode 22 and, via a second electrode conductor in the first lead 20, to the first pulse generator 26. A stimulation pulse to the right ventricle can be delivered to heart tissue by the first pulse generator via the first lead 20 and the first tip electrode 22. The stimulation pulse is then returned, via the first ring electrode 24 and the first lead 20, to the first pulse generator 26. Alternately, the stimulation pulse can be delivered via the first tip electrode 22 and an indifferent electrode 12 which, in this instance, consists of the enclosure of the heart stimulator 10 but can also consist of a separate electrode located somewhere in the body. The indifferent electrode 12 is connected to the first pulse generator 26 via an electric conductor 14 in order to return stimulation pulses from the right ventricle. A first detector 28 is connected in parallel across the output terminal of the first pulse generator 26 in order to sense right ventricular electrical activity in the heart.

In corresponding manner, a second tip electrode 82 is anchored in a wall of the right atrium RA of the heart 1 and connected, via an electrode conductor in the atrial lead 80, to a second pulse generator 36 in the heart stimulator 10. A second ring electrode 84 is located near the second tip electrode 82 and connected, via a further conductor in the second electrode lead 80, to the second pulse generator 36. Delivery of a stimulation pulse to the atrium can be bipolar via the second tip electrode 82 and the second ring electrode 84, or unipolar via the second tip electrode 82 and the indifferent electrode 12. A second detector 38 is connected in parallel across the output terminal of the second pulse generator 36 in order to sense atrial electrical activity in the right atrium of the heart. The pulse generators 26 and 36 and the detectors 28 and 38 are controlled by a control circuitry or control unit 40 which regulates the stimulation pulses with respect to amplitude, duration and stimulation interval, the sensitivity of the detectors 28 and 38 etc.

A physician using an extracorporeal programmer 44 can, via a telemetry unit 42 comprised in the heart stimulator 10, communicate with the heart stimulator 10 and thereby obtain information on identified conditions and also reprogram the different functions of the heart stimulator 10.

FIG. 3 further shows an embodiment of an analysis device. The analysis device 50 is connected via the atrial lead 80 to a sensor for sensing atrial mechanical activity, for instance in the form of an atrial wall motion sensor 81 for sensing atrial wall movements, or to an atrial pressure sensor 85 for sensing atrial pressure variations. Furthermore, the analysis device is further connected via the atrial lead 80 to a sensor for sensing atrial electrical activity, in this example the ring electrode 84. The analysis device 50 includes a measurement unit 52 which is capable of selectively receiving signals from any of the sensors, and which filters and amplifies the incoming signals in an appropriate manner.

The output signal from the measurement unit 52, is then sent to a buffer 54 and to a differentiating circuit 56. Buffering is performed so that the electrical activity signal is in phase with the mechanical activity signal when they are sent to a calculation unit 58. The calculation unit 58 calculates and identifies relevant information in the received sensor signals in view of the particular atrial arrhythmia detection criteria used in the stimulator for indicating atrial arrhythmia. Said relevant information could be any number of different characteristics, such as mechanical frequency, electrical frequency, measured amplitudes, relevant characteristics in the received signal, mechanical or electrical signal appearance or morphology, timing of particular events (P wave), etc.

The thus obtained relevant information from the signal holding information on mechanical and electrical activity is then sent to an evaluation unit 60, where the received information is evaluated and compared with selected threshold criteria. The selected threshold criteria could be values or levels that are pre-programmable and adjustable by a physician during follow-ups or by the stimulator itself, that are calculated by the stimulator after implantation, or that are a combination of both.

The output signal from the evaluation unit 60 comprises information of whether or not the respective evaluated signals, separately or in combination, indicate atrial arrhythmia. The output signal is forwarded to a mode switching unit 62 which communicates with the control unit 40. Thus, if the output signal from the evaluation unit 60 indicates atrial arrhythmia, the mode switching unit 62 checks whether the stimulator operates in a non-atrial tracking mode or in an atrial tracking mode, determines whether a mode switch is warranted, and if so, sends a signal to the control unit 40 to effectuate a mode switch.

Turning now to FIGS. 4-7, with reference also to FIGS. 1-3, there will be described different algorithms for determining an indication of atrial arrhythmia in accordance with different embodiments of the present invention. Even though these embodiments will be described separately, several or all of the algorithms thereof may be comprised in or utilized by one and the same stimulator. Furthermore, other complementary algorithms may also be comprised, such as an algorithm that strictly utilizes a sensed atrial IEGM signal as an electrical activity information signal for determining an indication of atrial arrhythmia. Since methods and algorithms for atrial arrhythmia detection and mode switch control based on electrical atrial activity alone are in regular use today in commercially available dual chamber pacemakers, use can be made of such a known method, providing that threshold criteria are set at a level such that appropriate specificity from that/those algorithm(s) alone is obtained.

Nevertheless, one example of such an electrical activity alone detection algorithm will briefly be described, without reference to any of the drawings. In this example, an atrial rate is calculated from a received atrial IEGM signal and compared to a selected threshold value, such as 160 atrial beats per minute. If the rate exceeds the threshold value, atrial tachyarrhythmia is indicated and a mode switch is triggered. The threshold value is selected in adaptation to the physiological needs of the patient, and possibly of the characteristics of the heart condition present. For example, the threshold value is set to a specific value lying between 130 and 200 atrial beats per minute. The threshold level could be preset and later adjusted, either by the physician at follow-ups, or by the stimulator in accordance with preprogrammed algorithms for arrhythmia detection threshold adjustment. Preferably, the algorithm monitors 3 to 10 successive atrial beats before an atrial arrhythmia is indicated and an ensuing mode switch is triggered.

Figure 4:
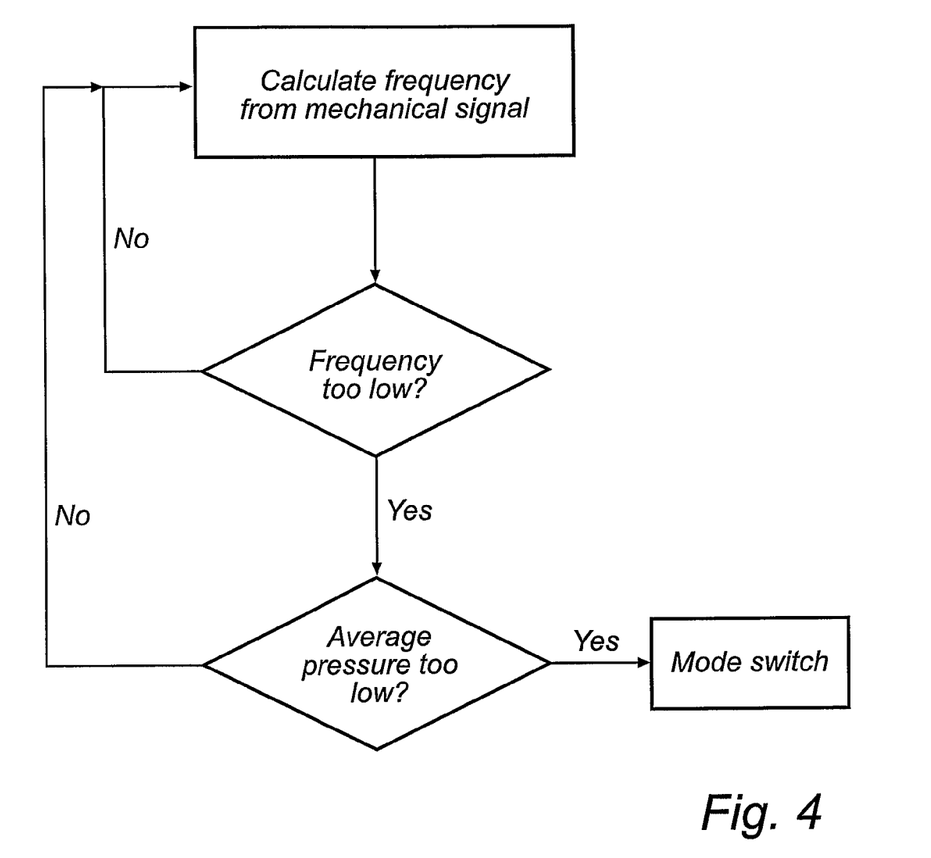
FIGS. 4-7 are flow diagrams illustrating mode switch triggering algorithms according to different exemplifying embodiments.

With reference to FIGS. 3 and 4, a detection algorithm for determining an indication of atrial tachyarrhythmia based on mechanical activity alone will now be described. First, the mechanical sensor 81, 85 provides a signal related to atrial mechanical activity. The signal is received by the measurement unit for appropriate filtering and amplification, and forwarded to the calculation unit 58, which calculates an atrial mechanical frequency or atrial rate. The object is to obtain a mechanical frequency which is directly related to and in correspondence with atrial contractions, e.g. by sensing pressure variations or cardiac wall movements representative of atrial contractions, for establishing an atrial heart rate. When the calculation unit 58 has calculated such a mechanical frequency, the evaluation unit compares the calculated frequency to a selected threshold value. If the calculated frequency exceeds the threshold value, an indication of atrial arrhythmia is output from the evaluation unit 60 to the mode switching unit 62, which triggers an ensuing mode switch if the stimulator is not already in a non-atrial tracking mode.

During for instance atrial fibrillation, AF, atrial contractions are essentially absent due to the chaotic nature of atrial tissue depolarization during AF. Then, absence of atrial mechanical contractions may be used as an indicator of atrial arrhythmia. Thus, the atrial tachyarrhythmia detection algorithm checks if the mechanical frequency falls below a selected threshold value, which is if the variations in atrial mechanical activity occur too seldom. In this embodiment, the algorithm then checks if the average amplitude of the mechanical activity, which in this embodiment is average atrial pulse pressure, is too low. This is done in order to differentiate true atrial arrhythmia with a situation where few or no contractions are detected due the set threshold level for sensing mechanical activity being too insensitive, such that even though the patient is in normal sinus rhythm, a low or no atrial rate is detected. If so, then the average mechanical activity should be within normal ranges and not too low. If the average mechanical activity, or average atrial pulse pressure, is determined to be within normal or acceptable ranges, the output signal of the evaluation unit will indicate that atrial tachyarrhythmia is not present.

According to a further embodiment (not illustrated) the calculated mechanical activity or atrial rate is also or alternatively compared to an upper threshold value, similar to the IEGM rate described above. If the rate exceeds the threshold value, which as an example may be the same as mentioned above, i.e. between 130 and 200 atrial beats per minute, atrial tachyarrhythmia is indicated as an output from the evaluation unit 60, which may trigger an ensuing mode switch depending on the current mode.

Figure 5:
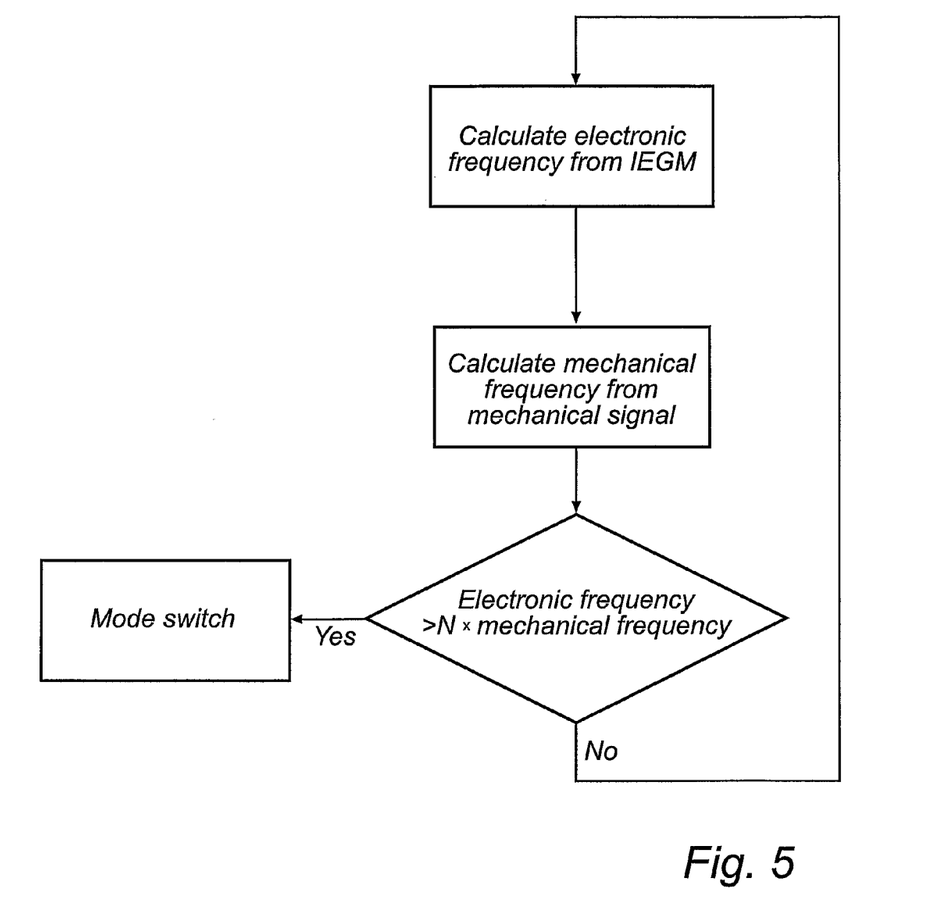

Turning to FIGS. 3 and 5, a first embodiment using a combination of information based on both detected electrical and mechanical activity for indicating atrial tachyarrhythmia will now be described. In this embodiment, a first signal related to atrial electrical activity is received by the measurement unit 52, as well as a second electrical signal related to atrial mechanical activity. The signals are appropriately filtered and amplified, and forwarded to a buffer 54 and a differentiating circuit 56 for bringing the two signals in phase. The signals are then forwarded to a calculation unit 58 which calculates an atrial electrical rate and an atrial mechanical rate, respectively, and forwards same calculated information as an output signal which is fed to the evaluating unit 60.

There, the respective calculated mechanical and electrical frequencies are compared to each other and the quotient therebetween is compared to a threshold value or range. If the quotient falls outside the threshold range, a signal indicating an atrial tachyarrhythmia is output by the evaluating circuit 60 and fed to the mode switch unit 62. Based on this signal and stored information regarding whether the stimulator is currently in an atrial tracking or a non-atrial tracking mode, the mode switching unit may effectuate a mode switch.

Figure 6:
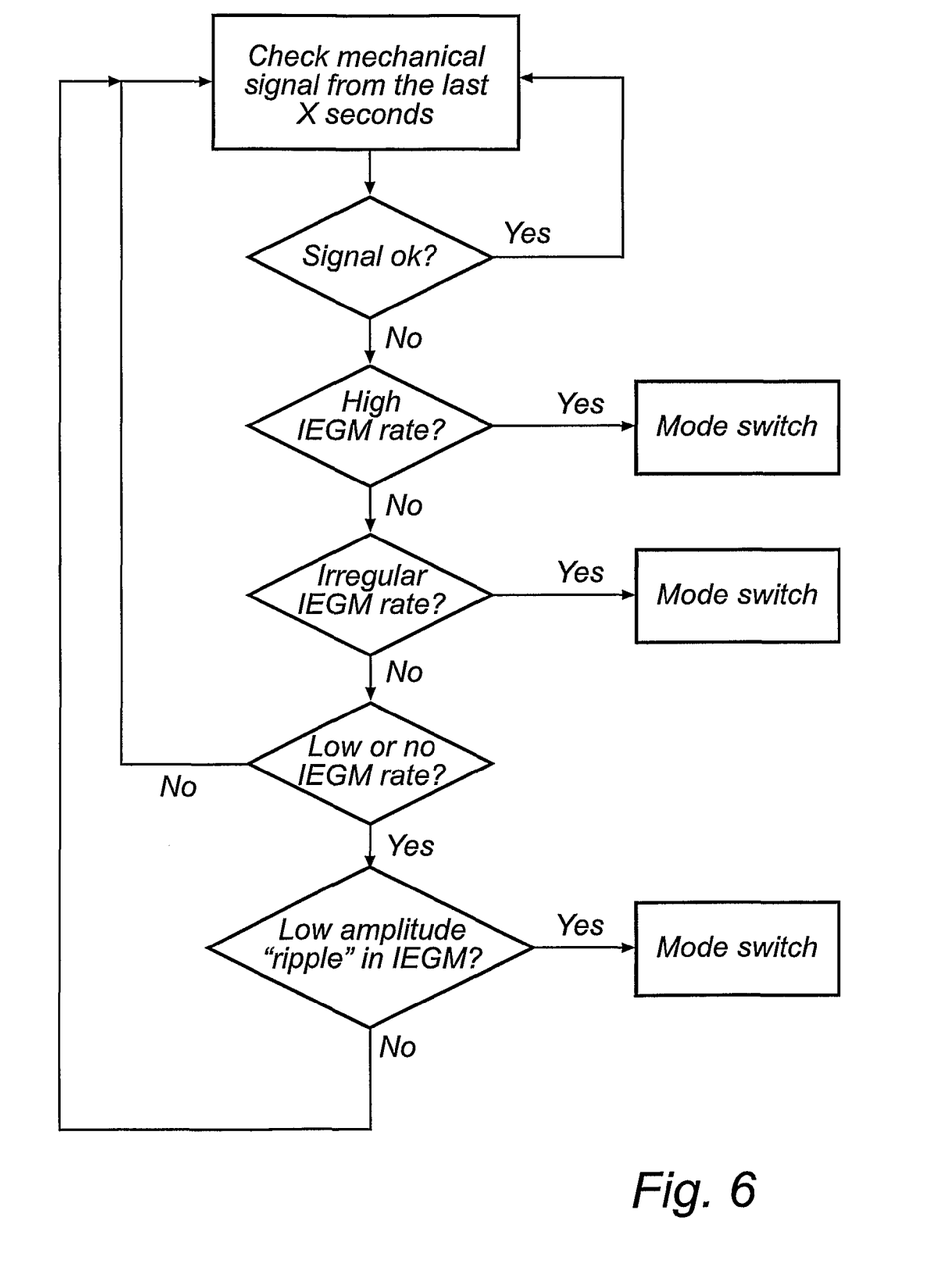

Turning now to another embodiment where a combination of mechanical and electrical activity information is utilized, with reference to FIGS. 3 and 6. In this embodiment, the appearance of a signal representative of mechanical activity is utilized. As a non-limiting example, a short sequence of about 2-5 seconds is studied. First, the signal is obtained through a pressure sensor arranged in an atrium of the heart 1 and received by the measurement unit 52 and subjected to appropriate signal processing. Then, the processed signal is received by the calculation unit 58, which determines the morphology of the mechanical activity signal. Alternatively, specific characteristics or features related to the appearance or morphology of the signal is calculated and determined. Information of said determined morphology or characteristics is/are then forwarded to an evaluation unit 60. There, this information is compared to reference information to determine if the mechanical activity signal appearance is within acceptable ranges. The reference information could be in the form of a reference template, typical reference characteristics, preset or adaptable reference values, or similar reference information which has been acquired when the patient is confirmed to be in normal sinus rhythm. If the evaluated information indicates a normal sinus rhythm, i.e. a stable atrium, no indication of atrial tachyarrhythmia is indicated and the detection algorithm returns to a state for receiving and evaluating new mechanical activity information.

However, if the answer to the check for a stable atrium is no, then an evaluation of the electrical activity signal ensues. In this embodiment, the IEGM rate is then studied in more detail. Preferably, and in order not to delay the arrhythmia detection procedure, a stored electrical activity signal representing the latest 3 to 10 seconds is studied. When a signal from a passed period is used, the signal has already been processed by the measuring unit 52, buffer 54, differentiating unit 56 and calculation unit 58, and the relevant calculated electrical activity information is received by the evaluating unit concurrently with the mechanical activity information, even if the time periods studied are not entirely overlapping. If the evaluation unit 60 determines that the electrical rate, i.e. IEGM rate, during the studied period exceeds a chosen threshold value, an indication of atrial arrhythmia is output to the mode switch unit 62, which then effectuates a mode switch if necessary.

If the electrical rate does not exceed a chosen threshold, a test for rate regularity is performed by the evaluating unit. The reason for the regularity check is that atrial fibrillation entails a variable IEGM signal amplitude, which can mean that not all oscillations are detected since the threshold level for the detection algorithm may be set above the amplitude for some atrial depolarization oscillations. If the evaluating circuit 60 determines the IEGM rate to be irregular, an indication of atrial arrhythmia is output to the mode switch unit 62.

Otherwise, then a check of the IEGM amplitude against a lower IEGM rate threshold is performed in order too determine if the electronic frequency is very low or if it is zero, i.e. no detections of electrical activity are made. If this is the case, then the cause may be atrial fibrillation with a very low amplitude, fine AF, or atrial standstill. If it is determined that the IEGM is not very low, the atrium is considered stable and no indication of atrial arrhythmia will be determined.

On the other hand, if the check for low or no IEGM rate results in a positive determination, the IEGM signal is searched for low amplitude ripple which is present during AF or fine AF, but not during standstill. This check for low amplitude ripple is in this embodiment made by studying the standard deviation of the IEGM signal. If the standard deviation of the IEGM is higher than a threshold value representing stable atrial activity, this would indicate an atrial tachyarrhythmia in the form of fine AF. If so, an indication of atrial arrhythmia is output by the evaluating circuit 60 to the mode switch unit 62. Alternatively, the lower threshold could be set at an even lower level at which fine AF ripple could be sensed. If significant electrical activity is determined with this lower threshold, then AF is indicated and an indication of atrial arrhythmia is output by the evaluating circuit 60.

Figure 7:
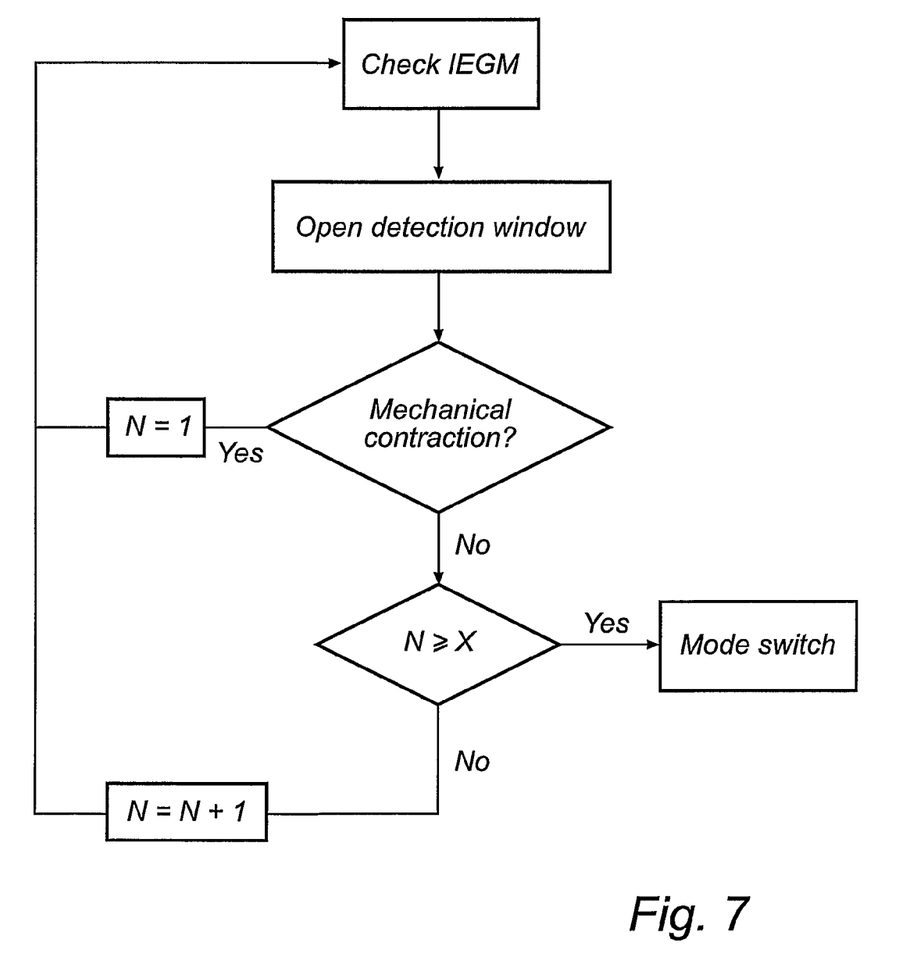

With reference to FIGS. 3 and 7, a further embodiment will now be described. According to this embodiment, an IEGM signal and a mechanical activity signal are first obtained in a similar manner as described above. The measurement unit 52, buffer 54 and differentiating circuit 56 processes the signals and outputs two time correlated signals representing atrial electrical and mechanical activity, respectively, to the calculation unit 58. There, the timing of the P wave in the IEGM signal is determined, and a mechanical activity detection window is applied to the mechanical activity based signal. Desired characteristics of the mechanical activity information within the detection window is then calculated by the calculation unit 58 and forwarded to the evaluation unit 60, which continuously receives said characteristics obtained during subsequent detection windows. If the evaluating unit 60, following comparison of the received information with reference information representing atrial contraction, determines that no atrial contraction is indicated during the detection window, then a check is made for how many consecutive latest detection windows no contraction has been indicated. If the present detection window represents a chosen number of consecutive detection windows where no indication of atrial contraction have been found, then an indication of atrial arrhythmia is determined and said indication is forwarded to the mode switching unit 62 for appropriate action. Preferably, the algorithm performs this determination of lacking atrial contraction for two to five successive detection windows, before an indication of atrial arrhythmia is determined.

In a further exemplifying embodiment, instead of determining for how many consecutive number of detection windows there are no atrial contractions, the evaluation may instead be made for a period corresponding to a selected number of subsequent detection windows, and atrial arrhythmia may be determined in the absence of at least a specified number of atrial contraction responses during that period. In other words, a period of 5 to 10 successive detection windows, i.e. P waves, may be evaluated, and atrial tachyarrhythmia indicated if 3 to 5 non-occurrences of atrial contraction occurs during this period.

In further embodiments of the present invention, the above mentioned algorithms for atrial arrhythmia detection may be used for determining when a mode switch from an non-atrial tracking mode back to an atrial tracking mode should be effectuated. Then, the atrial electrical and mechanical activity is continuously monitored during non-atrial tracking in order to assess when a return to atrial tracking mode is appropriate. According to these embodiments, all of the atrial arrhythmia detection algorithms used by the stimulator for determining when a mode switch away from atrial tracking mode should be performed, are also used in determining when a return mode switch back to atrial tracking mode is to be performed. The arrhythmia detection algorithms then operate in similar manner as described above, i.e. the electrical and mechanical activity information signals are received by the measuring unit 52, processed by the measuring unit 52, buffer 54, differentiating unit 56, calculating unit 58 and evaluation unit 60. If at least one of the detection algorithms utilizing mechanical, electrical or combination of mechanical and electrical activity information indicates atrial tachyarrhythmia, no mode switch back to atrial tracking will be effectuated. In other words, as long as not all of the atrial tachyarrhythmia detecting algorithms indicate stable atrial activity, the cardiac stimulator will remain in a non-atrial tracking mode.

According to further embodiments, additional criteria and atrial stability detection algorithms may be used as indicators for when a mode switch back to atrial tracking could or should be performed. Thus, when all of the atrial arrhythmia detecting algorithms indicate stable atrial activity, one or more further checks for the appropriateness of atrial tracking may be performed. Such additional atrial stability detection criteria could include the ventricular or atrial rate falling below a selected ventricular or atrial rate threshold, etc.

While the invention disclosed herein has been described by means of specific embodiments and applications thereof, numerous modifications and variations could be made therein by those skilled in the art without departing from the scope of the invention. Thus, it is to be understood that the above description of the invention and the accompanying drawings is to be regarded as a non-limiting example thereof, and that the scope of protection is defined by the appended patent claims.

The invention claimed is:

1. A device for a dual chamber cardiac stimulator for controlling the delivery of stimulation pulses to a human heart, wherein the stimulator is connectable to a lead arrangement arranged for sensing atrial electrical activity and atrial mechanical activity, the device comprising processing circuitry configured to:
receive a first signal representative of atrial electrical activity, and a second signal representative of atrial mechanical activity representative of atrial mechanical contractions;
determine if said electrical activity indicates atrial tachyarrhythmia, if said mechanical activity indicates atrial tachyarrhythmia, and if a combination of said electrical and mechanical activity indicates atrial tachyarrhythmia;
calculate, from said second signal, the frequency of mechanical activity, and compare said calculated mechanical frequency with a threshold value for determining if atrial tachyarrhythmia is indicated, compare said calculated mechanical frequency with an upper threshold value, with a lower threshold value, or both, determine that atrial tachyarrhythmia based on said mechanical activity is indicated if the calculated mechanical frequency is higher than said upper threshold value, or lower than said lower threshold value; and
effectuate a mode switch, as soon as at least said indication of atrial tachyarrhythmia based on said mechanical activity, from a first mode where delivery of ventricular stimulation pulses is synchronized to detected atrial events, to a second mode where delivery of ventricular stimulation pulses is unsynchronized to detected atrial events.

2. The device as claimed in claim 1, wherein said processing circuitry is configured to calculate from said first signal the frequency of atrial electrical activity, and compare said calculated electrical frequency with a threshold value for determining if atrial tachyarrhythmia is indicated.

3. The device as claimed in claim 1, wherein the processing circuitry is configured to:
detect from said first signal atrial depolarization,
detect from said second signal atrial contraction, and
determine that atrial tachyarrhythmia is indicated if detected atrial depolarization is not followed by a resulting mechanical contraction.

4. A device for a dual chamber cardiac stimulator for controlling the delivery of stimulation pulses to a human heart, wherein the stimulator is connectable to a lead arrangement arranged for sensing atrial electrical activity and atrial mechanical activity, the device comprising processing circuitry configured to:
receive a first signal representative of atrial electrical activity, and a second signal representative of atrial mechanical activity representative of atrial mechanical contractions;
determine if said electrical activity indicates atrial tachyarrhythmia, if said mechanical activity indicates atrial tachyarrhythmia, and if a combination of said electrical and mechanical activity indicates atrial tachyarrhythmia;
effectuate a mode switch, as soon as at least said indication of atrial tachyarrhythmia based on said mechanical activity, from a first mode where delivery of ventricular stimulation pulses is synchronized to detected atrial events, to a second mode where delivery of ventricular stimulation pulses is unsynchronized to detected atrial events;
calculate from said first signal the frequency of atrial electrical activity;
calculate from said second signal the frequency of atrial mechanical activity;
calculate a quotient between said electrical frequency and said mechanical frequency;
compare said quotient to a threshold range; and
determine that atrial tachyarrhythmia is indicated based on said electrical activity if the quotient falls outside said threshold range.

5. A device for a dual chamber cardiac stimulator for controlling the delivery of stimulation pulses to a human heart, wherein the stimulator is connectable to a lead arrangement arranged for sensing atrial electrical activity and atrial mechanical activity, the device comprising processing circuitry configured to:
receive a first signal representative of atrial electrical activity, and a second signal representative of atrial mechanical activity;
determine if said electrical activity indicates atrial tachyarrhythmia, if said mechanical activity indicates atrial tachyarrhythmia, and if a combination of said electrical and mechanical activity indicates atrial tachyarrhythmia;

effectuate a mode switch, as soon as either of said electrical, mechanical, or combination of electrical and mechanical activity indicates atrial tachyarrhythmia, from a first mode where delivery of ventricular stimulation pulses is synchronized to detected atrial events, to a second mode where delivery of ventricular stimulation pulses is unsynchronized to detected atrial events; and obtain the morphology or selected indicative features of said second signal, and evaluate said morphology or selected indicative features for determining if atrial tachyarrhythmia may be indicated.

6. The device as claimed in claim 5, wherein said processing circuitry is configured to:

evaluate, if said morphology or selected indicative features indicates that atrial tachyarrhythmia may be indicated, said first signal for determining if atrial tachyarrhythmia is indicated.

7. The device as claimed in claim 6, wherein said processing circuitry is configured to:

calculate from said first signal the frequency of atrial electrical activity, and evaluate said first signal and determining that atrial tachyarrhythmia is present if the frequency of atrial electrical activity exceeds a threshold value, or the frequency of atrial electrical activity is irregular.

8. A device for a dual chamber cardiac stimulator for controlling the delivery of stimulation pulses to a human heart, wherein the stimulator is connectable to a lead arrangement arranged for sensing atrial electrical activity and atrial mechanical activity, the device comprising processing circuitry configured to:

receive a first signal representative of atrial electrical activity, and a second signal representative of atrial mechanical activity representative of mechanical activity, wherein said atrial mechanical activity is atrial pressure changes detected by a pressure sensor, said pressure changes being representative of atrial contraction;

determine if said electrical activity indicates atrial tachyarrhythmia, if said mechanical activity indicates atrial tachyarrhythmia, and if a combination of said electrical and mechanical activity indicates atrial tachyarrhythmia; and effectuate a mode switch, as soon as either of said electrical, mechanical, or combination of electrical and mechanical activity indicates atrial tachyarrhythmia, from a first mode where delivery of ventricular stimulation pulses is synchronized to detected atrial events, to a second mode where delivery of ventricular stimulation pulses is unsynchronized to detected atrial events.

9. The device as claimed on claim 8, wherein the processing circuitry is configured to determine that atrial tachyarrhythmia is indicated if the amplitude of said detected pressure changes falls below a threshold value.

10. A device for a dual chamber cardiac stimulator for controlling the delivery of stimulation pulses to a human heart, wherein the stimulator is connectable to a lead arrangement arranged for sensing atrial electrical activity and atrial mechanical activity, the device comprising processing circuitry configured to:

receive a first signal representative of atrial electrical activity, and a second signal representative of atrial mechanical activity, wherein said atrial mechanical activity is atrial wall movements detected by an accelerometer, said atrial wall movements being representative of atrial contraction;

determine if said electrical activity indicates atrial tachyarrhythmia, if said mechanical activity indicates atrial tachyarrhythmia, and if a combination of said electrical and mechanical activity indicates atrial tachyarrhythmia; and effectuate a mode switch, as soon as either of said electrical, mechanical, or combination of electrical and mechanical activity indicates atrial tachyarrhythmia, from a first mode where delivery of ventricular stimulation pulses is synchronized to detected atrial events, to a second mode where delivery of ventricular stimulation pulses is unsynchronized to detected atrial events.

11. The device as claimed in claim 1, wherein said processing circuitry is configured to:

effectuate a mode switch from said second mode to said first mode if none of said mechanical, electrical and combination of mechanical and electrical activity indicates atrial tachyarrhythmia.

12. A dual chamber cardiac therapy system for delivering stimulation pulses to a human heart, comprising:

a pulse generator for generating said stimulation pulses;

control circuitry configured to receive a first signal representative of atrial electrical activity, and a second signal representative of atrial mechanical activity, determine if said electrical activity indicates atrial tachyarrhythmia, if said mechanical activity indicates atrial tachyarrhythmia, and if a combination of said electrical and mechanical activity indicates atrial tachyarrhythmia, and effectuate a mode switch, as soon as either of said electrical, mechanical, or combination of electrical and mechanical activity indicates atrial tachyarrhythmia, from a first mode where delivery of ventricular stimulation pulses is synchronized to detected atrial events, to a second mode where delivery of ventricular stimulation pulses is unsynchronized to detected atrial events; and a cardiac lead arrangement for conducting said stimulation pulses to the heart, and for conducting electrical signals from the heart to the control circuitry, said lead arrangement comprising an implantable lead arranged for sensing atrial electrical activity and atrial mechanical activity, said cardiac lead arrangement comprising a mechanical sensor that senses said atrial mechanical activity.

13. The system as claimed in claim 12, wherein said mechanical sensor is a pressure sensor arranged for positioning in or at an atrium of the heart.

14. The system as claimed in claim 12, wherein said mechanical sensor is an accelerometer.

15. A method for detecting an atrial arrhythmia for activating a pacing mode switch in a dual chamber cardiac stimulator, comprising the steps of:

receiving a first signal representative of atrial electrical activity, and a second signal representative of atrial mechanical activity, representing atrial mechanical contractions;

determining if said electrical activity indicates atrial tachyarrhythmia; if said mechanical activity indicates atrial tachyarrhythmia, and if a combination of said electrical and mechanical activity indicates atrial tachyarrhythmia;

calculating from said second signal the frequency of mechanical activity;

comparing said calculated mechanical frequency with a threshold value for determining if atrial tachyarrhythmia is indicated;

comparing said calculated mechanical frequency with an upper threshold value, with a lower threshold value, or both;

determining that atrial tachyarrhythmia is indicated if the calculated mechanical frequency is higher than said upper threshold value, or lower than said lower threshold value; and effectuating a mode switch, as soon as at least said indication of atrial tachyarrhythmia based on said mechanical activity, from a first mode where delivery of ventricular stimulation pulses is synchronized to detected atrial events, to a second mode where delivery of ventricular stimulation pulses is unsynchronized to detected atrial events.

16. The method as claimed in claim 15, further comprising the steps of calculating from said first signal the frequency of atrial electrical activity; and comparing said calculated electrical frequency with a threshold value for determining if atrial tachyarrhythmia is indicated.

17. The method as claimed in claim 15, further comprising the steps of:

detecting from said first signal atrial depolarization;

detecting from said second signal atrial contraction; and determining that atrial tachyarrhythmia is indicated if detected atrial depolarization is not followed by a resulting mechanical contraction.

18. A method for detecting an atrial arrhythmia for activating a pacing mode switch in a dual chamber cardiac stimulator, comprising the steps of:

receiving a first signal representative of atrial electrical activity, and a second signal representative of atrial mechanical activity, representing atrial mechanical contractions;

determining if said electrical activity indicates atrial tachyarrhythmia; if said mechanical activity indicates atrial tachyarrhythmia, and if a combination of said electrical and mechanical activity indicates atrial tachyarrhythmia;

calculating from said first signal the frequency of atrial electrical activity;

calculating from said second signal the frequency of atrial mechanical activity;

calculating a quotient between said electrical frequency and said mechanical frequency;

comparing said quotient to a threshold range;

determining that atrial tachyarrhythmia is indicated if the quotient falls outside said threshold range; and effectuating a mode switch, as soon as at least said indication of atrial tachyarrhythmia based on said mechanical activity, from a first mode where delivery of ventricular stimulation pulses is synchronized to detected atrial events, to a second mode where delivery of ventricular stimulation pulses is unsynchronized to detected atrial events.

19. A method for detecting an atrial arrhythmia for activating a pacing mode switch in a dual chamber cardiac stimulator, comprising the steps of:

receiving a first signal representative of atrial electrical activity, and a second signal representative of atrial mechanical activity, representing atrial mechanical contractions;

determining if said electrical activity indicates atrial tachyarrhythmia; if said mechanical activity indicates atrial tachyarrhythmia, and if a combination of said electrical and mechanical activity indicates atrial tachyarrhythmia;

obtaining the morphology or selected indicative features of said second signal;

evaluating said morphology or selected indicative features for determining if atrial tachyarrhythmia may be indicated; and effectuating a mode switch, as soon as at least said indication of atrial tachyarrhythmia based on said mechanical activity, from a first mode where delivery of ventricular stimulation pulses is synchronized to detected atrial events, to a second mode where delivery of ventricular stimulation pulses is unsynchronized to detected atrial events.

20. The method as claimed in claim 19, further comprising the step of evaluating, if said morphology or selected indicative features indicates that atrial tachyarrhythmia may be indicated, said first signal for determining if atrial tachyarrhythmia is indicated.

21. The method as claimed in claim 20, further comprising the steps of calculating from said first signal the frequency of atrial electrical activity; and evaluating said first signal and determining that atrial tachyarrhythmia is present if the frequency of atrial electrical activity exceeds a threshold value, or the frequency of atrial electrical activity is irregular.

22. A method for detecting an atrial arrhythmia for activating a pacing mode switch in a dual chamber cardiac stimulator, comprising the steps of:

receiving a first signal representative of atrial electrical activity, and a second signal representative of atrial mechanical activity, representing atrial mechanical contractions, wherein said atrial mechanical activity is atrial pressure changes detected by a pressure sensor, said pressure changes being representative of atrial contraction; wherein said atrial mechanical activity is atrial pressure changes detected by a pressure sensor, said pressure changes being representative of atrial contraction;

determining if said electrical activity indicates atrial tachyarrhythmia; if said mechanical activity indicates atrial tachyarrhythmia, and if a combination of said electrical and mechanical activity indicates atrial tachyarrhythmia;

effectuating a mode switch, as soon as at least said indication of atrial tachyarrhythmia based on said mechanical activity, from a first mode where delivery of ventricular stimulation pulses is synchronized to detected atrial events, to a second mode where delivery of ventricular stimulation pulses is unsynchronized to detected atrial events.

23. The method as claimed in claim 22, comprising the step of determining that atrial tachyarrhythmia is indicated if the amplitude of said detected pressure changes falls below a threshold value.

24. A method for detecting an atrial arrhythmia for activating a pacing mode switch in a dual chamber cardiac stimulator, comprising the steps of:

receiving a first signal representative of atrial electrical activity, and a second signal representative of atrial mechanical activity, representing atrial mechanical contractions, wherein said atrial mechanical activity is atrial wall movements detected by an accelerometer, said atrial wall movements being representative of atrial contraction;

determining if said electrical activity indicates atrial tachyarrhythmia; if said mechanical activity indicates atrial tachyarrhythmia, and if a combination of said electrical and mechanical activity indicates atrial tachyarrhythmia;

effectuating a mode switch, as soon as at least said indication of atrial tachyarrhythmia based on said mechanical activity, from a first mode where delivery of ventricular stimulation pulses is synchronized to detected atrial events, to a second mode where delivery of ventricular stimulation pulses is unsynchronized to detected atrial events.

25. The method as claimed in claim 15, further comprising the step of effectuating a mode switch from said second mode to said first mode if none of said mechanical, electrical and combination of mechanical and electrical activity indicates atrial tachyarrhythmia.

* * * * *